United States Patent [19]

Paust

[11] 4,044,026

[45] Aug. 23, 1977

[54] SUBSTITUTED SUCCINALDEHYDE MONOACETALS

[75] Inventor: Joachim Paust, Neuhofen, Germany

[73] Assignee: BASF Aktiengesellschaft, Ludwigshafen, Rhine, Germany

[21] Appl. No.: 523,442

[22] Filed: Nov. 13, 1974

[30] Foreign Application Priority Data

Nov. 24, 1973 Germany .............................. 2358690

[51] Int. Cl.$^2$ ....................... C07C 45/00; C07C 47/02
[52] U.S. Cl. .......................... 260/340.9 R; 260/600 R; 260/340.7; 260/602; 260/615 A; 252/522; 260/473 G; 260/484 R; 424/341; 424/342; 424/308; 424/312
[58] Field of Search .................... 260/602, 600, 340.9, 260/611 V, 600 R

[56] References Cited

PUBLICATIONS

Hattori, Chemical Abstracts, vol. 55 (1961) 20928b).
Slama et al., Proceedings of the National Academy of Sciences (1965) vol. 54, p. 413.
Slama, Annual Review of Biochemistry, vol. 40 (1971) p. 1098.
Sarmiento et al., Science, vol. 179 (1973) p. 1342.

Primary Examiner—Bernard Helfin
Attorney, Agent, or Firm—Keil, Thompson & Shurtleff

[57] ABSTRACT

New substituted succinaldehyde monoacetals which are produced by introducing an $\alpha, \beta$-unsaturated aldehyde bearing halogen, arylsulfonyl or alkylsulfonyl as a substituent in the $\gamma$-position into a solution of an alkali metal alcoholate, an alkali metal glycolate or an alkali metal phenolate in a lower alcohol at a temperature of less than 50° C. The new succinaldehyde monoacetals are of great interest as intermediates in the production of perfumes and of terpene derivatives of the type of juvenile hormones.

2 Claims, No Drawings

SUBSTITUTED SUCCINALDEHYDE MONOACETALS

The invention relates to substituted succinaldehyde monoacetals of the general formula (I):

(I)
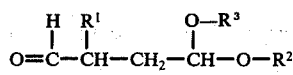

in which
R¹ is alkyl of one to four carbon atoms or phenyl;
R² is alkyl of one to four carbon atoms or phenyl;
R³ is alkyl of one to four carbon atoms; and
R² and R³ together may be ethylene which may bear alkyl as a substituent.

The new compounds are of great interest as intermediates for the production of perfumes and of terpene derivatives of the juvenile hormone type. For example the aldehydes of formula (I) may be reacted in a simple manner with the known phosphorus ylids of the formulae (III) and (IV):

(III)
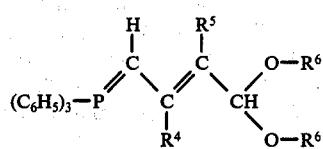

(IV)
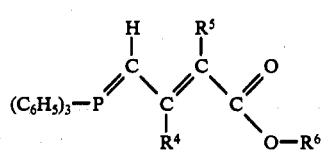

in which R⁴ and R⁵ are H, CH₃ or C₂H₅ and R⁶ is alkyl of one to four carbon atoms. The substituted octadiene bisacetals and octadiene ester acetals obtained in this reaction are suitable for controlling insects. Their good insecticidal effect is obviously attributable to a juvenile hormone effectiveness for they are mainly used during the larval or pupal stage on the immature insect so that they affect the metamorphosis and cause abnormal growth leading to infertility or to death.

Acetals of compounds (I) with 1,3-diols have particular odorant properties. Their odor is reminiscent of cinnamon or hay. These compounds harmonize particularly well in compositions with coumarins and ionones and they also exhibit fixing properties. Among these bisacetals the compounds of formula (I) with 3-methyl-butane-1,3-diol and 2,2-dimethylpropane-1,3-diol are stressed. They are obtained in a simple manner by mixing compounds of formula (I) with 1,3-diols in a solvent such as benzene in the presence of a 4 A molecular sieve.

Succinaldehyde monoacetals of the formula (I)

(I)
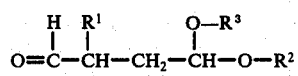

in which
R¹ is hydrogen, alkyl of one to 10 carbon atoms and preferably one to four carbon atoms, cycloalkyl of five to seven carbon atoms, phenyl or phenyl bearing alkyl as a substituent;
R² is alkyl of one to four carbon atoms or phenyl;
R³ is alkyl of one to four carbon atoms; and
R² and R³ together may also be an ethylene group which may bear alkyl as a substituent;
may be prepared in a notable reaction by introducing an α,β-unsaturated aldehyde of the general formula (II):

(II)

in which R¹ has the above meanings and X is halogen, arylsulfonyloxy or alkylsulfonyloxy and preferably chlorine, bromine or methylsulfonyloxy into a solution of an alkali metal alcoholate, an alkali metal glycolate or an alkali metal phenolate in an alcohol of one to four carbon atoms so that the temperature of the reaction mixture if possible does not exceed 50° C and allowing the reaction mixture to complete reaction.

The α,β-unsaturated aldehydes of formula (II) required as starting compounds can be prepared in a simple manner in good yields. For example 2-methyl-4-chloro-2-butenal is obtained by reaction of 2-formyl-2-hydroxy-3-butene with thionyl chloride or phosgene in the presence of a tertiary amine according to German Pat. No. 1,188,577. 2-Ethyl-4-chloro-2-butenal is obtained for example by the reaction of an acetal of 2-oxobutanal with vinyl magnesium chloride, and rearrangement of the resulting 2-hydroxy-2-vinyl-butanal with thionyl chloride in dimethylformamide followed by hydrolysis of the 2-ethyl-4-chloro-2-buten-1-al. The acetals of 2-oxobutanal required for this purpose are obtained for example according to German Pat. No. 835,594 from butynediol.

2-methyl-4-methylsulfonyloxy-2-butenal is obtained from 2-methyl-4-acetoxy-2-butenal (which can be prepared according to DAS 1,227,000) by acetalization, base-catalyzed transesterification of the acetal acetate in methanol into the acetal of 2-methyl-4-hydroxy-2-butenal, hydrolytic elimination of the acetal function under mild conditions and mesylation of the resulting 2-methyl-4-hydroxy-2-butenal by a conventional method.

Particularly suitable examples of α,β-unsaturated aldehydes of the formula (II) are:
2-methyl-4-chloro-2-butenal,
2-methyl-4-bromo-2-butenal, 2-methyl-4-mesyloxy-2-butenal,
2-ethyl-4-chloro-2-butenal,
2-phenyl-4-chloro-2-butenal and
2-phenyl-4-bromo-2-butenal.

Particularly suitable alkali metal alcoholates and alkali metal glycolates are the alcoholates of sodium, potassium or lithium with alcohols of one to four and preferably one or two carbon atoms. Specific examples are NaOCH₃, KOCH₃, LiOCH₃, NaOC₂H₅, KOC₂H₅, NaO-i-C₃H₇, NaO-n-C₄H₉, NaO-i-C₄H₉, KO-i-C₄H₉, KO-i-C₃H₇ and NaO-CH₂-CH₂ONa. The reaction does not take place with KO-t-C₄H₉ in t-butanol.

Potassium phenolate and sodium phenolate are preferred as alkali metal phenolates.

Methanol, ethanol, n-propanol, isopropanol, ethylene glycol and also n-butanol and isobutanol are suitable as alcohols of one to four carbon atoms.

The reaction takes place according to the following equation:

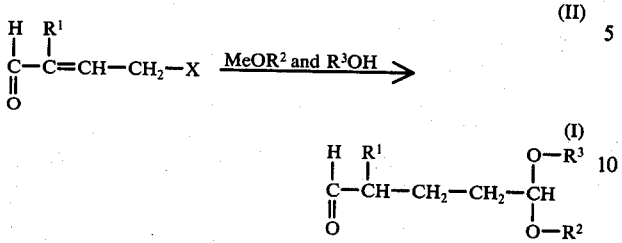

in which $R^1$, $R^2$ and $R^3$ have the meanings given above and Me is an alkali metal.

A convenient procedure for carrying out the invention is by slowly introducing the $\alpha,\beta$-unsaturated aldehyde of the formula (II) to an about 1M to 2M alcoholic solution of the alkali metal alcoholate, glycolate or phenolate, slight heating thus taking place. The best yields are achieved when the reaction mixture heats up only to 40° C. The reaction mixture may then be kept at a temperature of up to 50° C while mixing intensely, for example by stirring. The reaction mixture has fully reacted after from about 30 minutes to 1 hour.

The alkali metal alcoholate, glycolate or phenolate is generally used in an amount of from 1 to 1.4 val and preferably from 1.1 to 1.2 val per mole of aldehyde of formula (II) in the form of a from 1M to 2M solution in alcohol. It is possible to add inert solvent to the alkaline alcoholate or phenolate solution provided it does not result in any appreciable decrease in the solubility of the alkali metal alcoholate, but in most cases such addition is not necessary and may even result in a decrease in the yield.

Examples of inert solvents which it is possible to use are dimethylformamide, tetrahydrofuran, dioxane and dichloroethylene.

The reaction mixture is processed by a conventional method, for example by mixing it with water and a solvent having little or no miscibility with water such as methylene chloride, benzene, toluene, chlorobenzene or diethyl ether followed by phase separation. The crude product may be obtained in pure form by fractionation at subatmospheric pressure.

New substances which are of interest as immediate precursors of compounds having juvenile hormone activity can be prepared by means of the process according to the invention simply and in very good yields from fairly easily accessible compounds. The new compounds in the form of their acetals with 1,3-diols also have interesting perfume properties.

The following Examples illustrate the invention.

EXAMPLE 1

16.3 g (0.1 mole) of 2-methyl-4-bromo-2-butenal is dripped with 10 minutes at ambient temperature into a solution of 6.5 g (0.12 mole) of sodium methylate in 60 ml of methanol. The temperature slowly rises to about 40° C. The whole is stirred for another hour, 200 ml of water and 100 ml of methylene chloride are added to the reaction mixture and the methylene chloride phase is separated.

After the solvent has been distilled off, 14.0 g of 2-methyl- 4,4-dimethoxybutanal is obtained which according to gas chromatographic analysis has a purity of about 95%. The crude product can be purified by distillation at subatmospheric pressure.

12.9 g of a product having a boiling point of from 38° to 40° C at 0.2 mm is obtained. This is equivalent to a yield of 88% of theory. The nmr-spectroscopic data are particularly relevant in proving the structure:

$$H-C^1-C^2H-C^3H_2-C^4H-OC^6H_3$$
$$\overset{\|}{O} \quad \overset{|}{C^5H_3} \quad \overset{|}{O}$$
$$\overset{|}{CH_3}$$

| | |
|---|---|
| $C^1H$ d 9.65 | ppm.J 2 Hz |
| $C^2H$ m 2 - 2.5 | ppm |
| $C^3H_2$ m 1.3 - 2.0 | ppm |
| $C^4H$ t 4.28 | ppm, J 5 Hz |
| $C^5H_3$ d 0.89 | ppm, J 7 Hz |
| $C^6H_3$ s 3.12 | ppm. |

EXAMPLE 2

11.9 g (0.1 mole) of 2-methyl-4-chloro-2-butenal is dripped within about 10 minutes into 60 ml of an about 2M solution of sodium methylate in methanol at ambient temperature.

The solution warms up slowly to about 40° C. After an hour 200 ml of water and 100 ml of methylene chloride are added. After the methylene chloride phase has been separated and concentrated there remains 14.4 g of 2-methyl-4,4-dimethoxybutanal of which the purity is determined as about 96% by gas chromatography. Distillation at subatmospheric pressure gives 13.3 g of an analytically pure product of the boiling point 38° to 41° C at 0.2 mm. This is equivalent to a yield of 91% of theory.

EXAMPLE 3

16.3 g (0.1 mole) of 2-methyl-4-bromo-2-butenal is dripped at ambient temperature into a solution of 2.8 g of sodium (0.12 gram atom) in 60 ml of ethanol. Reaction proceeds with a slight rise in temperature. Sodium bromide is thus thrown down as a white precipitate. After about an hour the reaction mixture is worked up by partition between methylene chloride and water analogously to Example 1. After the methylene chloride phase has been concentrated 17.7 g of 2-methyl-4,4-diethoxybutanal is obtained as a pale yellow oil of which the gas chromatographic purity is 91%. Distillation at strongly subatmospheric pressure gives 15.0 g of the substance in analytically pure form with a boiling point of 41° to 45° C at 0.2 mm. This is equivalent to a yield of 86% of theory.

EXAMPLE 4

The procedure described in Example 3 is repeated but 11.9 g of 2-methyl-4,4-diethoxy-2-butenal is used insteat of 16.3 g of 2-methyl- 4-bromo-2-butenal. Pure 2-methyl-4,4-diethoxybutanal is obtained in a yield of 89% of theory.

EXAMPLE 5

2.8 g (0.12 mole) of sodium is dissolved in the necessary amount of isopropanol. 11.8 g (0.1 mole) of 1-methyl-4-chloro-2-butenal is dripped into this solution at ambient temperature while stirring. The reaction proceeds with a slight rise in temperature and the precipitation of sodium chloride. The mixture is kept for an hour at 40° C, 200 of ml of water and 100 ml of benzene are added, the whole is mixed and the benzene phase is separated. After the benzene has been removed in a rotational evaporator 22.2 g of 2-methyl-4,4-di- isopropoxy-butanal is obtained as residue; according to gas chromatographic investigation this has a purity of about 88%. Fractional distillation gives 16.4 g of an analytically pure product having a boiling point of from 44° to 47° C at 0.2 mm. This is equivalent to a yield of 81% of theory.

EXAMPLE 6

The procedure described in Example 2 is repeated but 0.1 mole (13.3 g) of 2-ethyl-4-chloro-2-butenal is used instead of 0.1 mole of 2-methyl-4-chloro-2-butenal. Crude 2-ethyl-4,4-dimethyoxybutanal is obtained with a purity of 92% (determined by gas chromatography). Distillation at subatmospheric pressure gives 14.4 g of a pure substance of the boiling point 40° to 43° at 0.2 mm. This is equivalent to a yield of 90% of theory.

EXAMPLE 7

18 g (0.1 mole) of 2-phenyl-4-chloro-2-butenal is dripped at 40° C while stirring into a solution of 2.8 g (0.12 gram atom) of sodium in 80 ml of methanol. The whole is stirred for another hour at 40° C and is then worked up in the manner described in Example 5 by partition between benzene and water. After the benzene phase has been concentrated 23.1 g of 2-phenyl-4,4-dimethoxybutanal of a purity of about 87% (determined by gas chromatography) remains behind. Fractional distillation at strongly subatmospheric pressure gives 17.1 g of an analytically pure preparation having a boiling point of 78° to 83° C at 0.2 mm. This is equivalent to a yield of 82% of theory.

EXAMPLE 8

118 g (1 mole) of 2-methyl-4-chloro-2-butenal is dripped into a solution of 8.4 g of lithium in 600 ml of methanol while stirring. The reaction proceeds with a slight rise in temperature to 45° C and takes 90 minutes. The solution is then worked up conventionally by partition between methylene chloride and water. After the methylene chloride has been removed in a rotational evaporator there is obtained as a residue 156 g of a pale yellow oil which according to gas chromatographic and nmr-spectroscopic analysis consists to the extent of 92% of 2-methyl-4,4-dimethoxybutanal. Fractional distillation at subatmospheric pressure gives 138.7 of the product in analytically pure form with a boiling point of from 44° to 48° C. This is equivalent to a yield of 95% of theory.

EXAMPLE 9

11.8 g (0.1 mole) 2-methyl-4-chloro-2-butenal is dripped at ambient temperature into a solution of 10.4 g (0.13 mole) of potassium methylate in 60 ml of methanol and the whole is stirred for an hour. The product is worked up as described in Example 1. 10.5 g of 2-methyl-4,4-dimethoxybutanal is obtained by distillation at subatmospheric pressure. According to gas chromatographic and nmr analysis it has a purity of more than 98%. The yield is 72% of theory.

EXAMPLE 10

11.8 g (0.1 mole) of 2-methyl-4-chloro-2-butenal is dripped into 120 ml of a 2M solution of sodium phenolate in methanol. The reaction proceeds with a slight rise in temperature. The whole is stirred for another hour at 40° C and then worked up by partition between benzene and water. When the benzene phase is concentrated there remains as a residue 16.4 g of crude 2-methyl-4-methoxy-4- phenoxybutenal having a purity of about 80%. 12.1 g of a pure product having a boiling point of from 84° at 0.5 mm is obtained by distillation at strongly subatmospheric pressure. The yield is 58% of theory.

EXAMPLE 11

17.8 g (0.1 mole) of 2-methyl-4-mesylosy-2-butenal is dripped at ambient temperature into a solution of 6.5 g (0.12 mole) of sodium methylate in 60 ml of methanol while stirring. The reaction proceeds with a slight rise in temperature and is over after about an hour. The mixture is worked up in a conventional manner by adding water and methylene chloride. The solvent is removed from the methylene chloride phase and 13.8 g of 2-methyl-4,4-dimethoxybutanal is obtained in a purity of about 91%. Distillation at subatmospheric pressure gives 12 g of the analytically pure product having a boiling point of 41° to 44° C at 0.4 mm. This is equivalent to a yield of about 82% of the theory.

EXAMPLE 12

10.4 g (0.1 mole) of 4-chloro-2-buten-1-al is dripped into 120 ml of a 1M solution of sodium methylate in methanol while stirring. The temperature rises temporarily to 44° C. After a reaction period of 45 minutes the reaction mixture has 200 ml of water added to it and the whole is extracted three times with 100 ml of methylene chloride. The methylen chloride phase is concentrated and 16.2 g of a yellow oil is obtained which according to gas chromatographic analysis has a content of 78% of 4,4-dimethoxy-butanal. Fractional distillation gives 9.5 g of a pure product having a boiling point of from 46° to 49° C at 2.5 mm. The yield is thus 72% of theory.

EXAMPLE 13

11.9 g (0.1 mole) of 2-methyl-4-chloro-2-butenal is dripped at ambient temperature into a solution of 2.8 g (0.12 gram atom) of sodium in 100 ml of dry ethylene glycol while stirring. The temperature of the solution rises temporarily to 42° C. Forty-five minutes later 200 ml of water is added to the reaction mixture which is then extracted three times with 100 ml of methylene chloride. Upon evaporation of the methylene chloride phase 18 g of a yellow oil is obtained which contains the desired 2-methylbutane-1,4-dial-4- ethylene acetal together with high boiling point constituents of unknown structure. 7.9 g of a pure product having a boiling point of 44° to 46° C at 0.5 mm is obtained by fractional distillation. This is equivalent to a yield of 55%.

I claim:

1. 2-Methyl-4-methoxy-4-phenoxybutanal.
2. A process for the production of a succinaldehyde monoacetal of the formula (I):

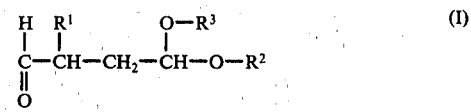

in which
R[1] is hydrogen, alkyl of one to 10 carbon atoms, cycloalkyl of five to seven carbon atoms, phenyl, or phenyl bearing alkyl as a substituent;
R[2] is alkyl of one to four carbon atoms or phenyl;

$R^3$ is alkyl of one to four carbon atoms; and $R^2$ and $R^3$ may together by an ethylene group which may bear alkyl as a substituent;

wherein an α,β-unsaturated aldehyde of the formula (II):

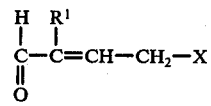

in which $R^1$ has the above meanings and X is chlorine, bromine or methylsulfonyloxy is introduced into a solution of an alkali metal alcoholate, an alkali metal glycolate or an alkali metal phenolate in an alcohol of one to four carbon atoms so that the temperature of the reaction mixture does not rise substantially above 50° C and the reaction mixture is allowed to complete the reaction.

* * * * *